United States Patent
Choi et al.

(10) Patent No.: US 12,016,667 B2
(45) Date of Patent: **\*Jun. 25, 2024**

(54) APPARATUS AND METHOD FOR OBTAINING BIO-INFORMATION

(71) Applicant: SAMSUNG ELECTRONICS CO., LTD., Suwon-si (KR)

(72) Inventors: Chang Mok Choi, Suwon-si (KR); Byung Hoon Ko, Hwaseong-si (KR); Jong Wook Lee, Suwon-si (KR); Youn Ho Kim, Hwaseong-si (KR); Young Soo Kim, Seoul (KR); Jeong Eun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 306 days.

This patent is subject to a terminal disclaimer.

(21) Appl. No.: 17/540,799

(22) Filed: Dec. 2, 2021

(65) Prior Publication Data
US 2022/0087556 A1 Mar. 24, 2022

Related U.S. Application Data
(63) Continuation of application No. 16/254,004, filed on Jan. 22, 2019, now Pat. No. 11,213,216.

(30) Foreign Application Priority Data
Jul. 13, 2018 (KR) .......................... 10-2018-0081690

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0075* (2013.01); *A61B 5/0082* (2013.01);
(Continued)

(58) Field of Classification Search
None
See application file for complete search history.

(56) References Cited

U.S. PATENT DOCUMENTS 11,213,216 B2 * 1/2022 Choi .................. A61B 5/02125
2009/0182240 A1 7/2009 Jang et al.
(Continued)

FOREIGN PATENT DOCUMENTS

KR 10-2008-0074623 A 8/2008
KR 10-2010-0018127 A 2/2010
(Continued)

OTHER PUBLICATIONS

Communication dated Sep. 9, 2023 issued by the Korean Patent Office in KR Patent Application No. 10-2018-0081690.

*Primary Examiner* — Jonathan Cwern
(74) *Attorney, Agent, or Firm* — Sughrue Mion, PLLC

(57) ABSTRACT

An apparatus for obtaining bio-information may include a pulse wave sensor including a light source and a detector. The light source is configured to emit multi-wavelength light to an object of interest and the detector is configured to detect light reflected from the object. In addition, the apparatus may include a processor configured to obtain a change in volume of a blood vessel based on one or more of quantity of detected multi-wavelength light and absorbance coefficients of respective wavelengths of the multi-wavelength light and obtain bio-information based on the measured change in volume of the blood vessel.

20 Claims, 17 Drawing Sheets

(51) Int. Cl.
*A61B 5/021* (2006.01)
*A61B 5/026* (2006.01)

(52) U.S. Cl.
CPC ........ *A61B 5/02125* (2013.01); *A61B 5/6826* (2013.01); *A61B 5/0261* (2013.01)

(56) References Cited

U.S. PATENT DOCUMENTS

| | | |
|---|---|---|
| 2010/0036265 A1 | 2/2010 | Kim et al. |
| 2014/0014151 A1 | 4/2014 | Miller |
| 2014/0114151 A1* | 4/2014 | Miller ................. A61B 5/1477 600/309 |
| 2015/0238095 A1 | 8/2015 | Lading et al. |
| 2016/0113589 A1 | 4/2016 | Yoon |
| 2017/0071550 A1 | 3/2017 | Newberry |
| 2017/0172430 A1 | 6/2017 | Zhao et al. |
| 2017/0172431 A1 | 6/2017 | Kim et al. |
| 2017/0209055 A1* | 7/2017 | Pantelopoulos ... A61B 5/02438 |
| 2017/0258340 A1 | 9/2017 | Przybyszewski et al. |
| 2017/0303800 A1 | 10/2017 | Flower et al. |
| 2018/0055364 A1 | 3/2018 | Pierro |

FOREIGN PATENT DOCUMENTS

| | | |
|---|---|---|
| KR | 10-2016-0047838 A | 5/2016 |
| KR | 10-1638381 B1 | 7/2016 |
| KR | 10-2016-0123321 A | 10/2016 |
| KR | 10-2017-0066600 A | 6/2017 |
| WO | 2007/097702 A1 | 8/2007 |
| WO | 2017/156501 A1 | 9/2017 |

* cited by examiner

APPARATUS AND METHOD FOR OBTAINING BIO-INFORMATION

CROSS-REFERENCE TO RELATED APPLICATION(S)

This application is a continuation application of U.S. application Ser. No. 16/254,004, filed on Jan. 22, 2019, which is now U.S. Pat. No. 11,213,216 B2 issued on Jan. 4, 2022, which claims priority from Korean Patent Application No. 10-2018-0081690, filed on Jul. 13, 2018, in the Korean Intellectual Property Office, the entire disclosures of which are incorporated herein by reference for all purposes.

BACKGROUND

1. Field

Apparatuses and methods consistent with exemplary embodiments relate to an apparatus and a method for measuring bio-information, and more particularly, to a technology for measuring blood pressure in a non-intrusive manner using a multi-wavelength photoplethysmography (PPG) signal.

2. Description of Related Art

General techniques for non-invasive extraction of cardiovascular features without the use of a compression cuff include pulse wave analysis and pulse wave velocity measurement.

The pulse wave analysis is a method of extracting cardiovascular characteristics by analyzing the shape of a photoplethysmography (PPG) or a body surface pressure signal obtained from a peripheral part of a body, such as a fingertip, a radial artery, or the like. Blood ejected from the left ventricle causes reflection at the sites of large branches, such as the renal arteries and the lower aorta, which affects the shape of the PPG or a body surface pressure wave measured at the peripheral part of a body. Accordingly, by analyzing the shape of the pulse wave, it is possible to estimate a degree of arteriosclerosis, vascular age, aortic pressure waveform, or the like.

The pulse wave velocity measurement is a method of extracting cardiovascular characteristics, such as a degree of arteriosclerosis, blood pressure, or the like, by measuring a pulse wave propagation time, wherein a pulse transit time (PTT) between an R peak (left ventricular contraction interval) of an electrocardiogram (ECG) and a PPG is measured by measuring the ECG and the PPG at the peripheral part of a body and a velocity at which the blood from the heart reaches the peripheral part of the body is calculated by dividing an approximate length of an arm by the measurement result.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, there is provided an apparatus for obtaining bio-information, including: a pulse wave sensor including a light source and a detector, the light source configured to emit multi-wavelength light to an object, the detector configured to detect the multi-wavelength light reflected from the object; and a processor configured to obtain a change in volume of a blood vessel based on one or more of a quantity of the detected multi-wavelength light and absorbance coefficients of respective wavelengths of the multi-wavelength light and obtain the bio-information based on the change in volume of the blood vessel.

The processor may obtain the change in volume of the blood vessel based on a difference between a value, obtained by multiplying a quantity of detected light of a first wavelength of the multi-wavelength light by a ratio of an absorbance coefficient of the first wavelength and an absorbance coefficient of a second wavelength of the multi-wavelength light, and a quantity of light of the second wavelength.

The processor may differentiate, with respect to time, the difference between the value, obtained by multiplying the quantity of detected light of the first wavelength by the ratio of the absorbance coefficient of the first wavelength and the absorbance coefficient of the second wavelength, and the quantity of light of the second wavelength, and obtain the change in volume of the blood vessel based on a differential value.

The processor may generate a graph of the differential value against time and monitor a time interval during which the volume of the blood vessel is changed according to a change in transmural pressure.

The processor may detect one or more peaks based on the differential value and obtain the bio-information using the detected one or more peaks.

The processor may detect, as a peak, a point at which the differential value is greater than a first threshold and a sharpness is greater than a second threshold.

The processor may determine, as a sharpness at a first point, determine a cosine value of an angle, formed between a second point and a third point, the second point and the third point being on a left and a right of the first point.

The processor may extract one or more features based on the detected one or more peaks and force information about a force applied to the pulse wave sensor by the object.

The apparatus may further include a force sensor configured to acquire the force information about the force applied to the pulse wave sensor by the object.

The processor may provide guidance information about a magnitude of force to be applied to the pulse wave sensor in response to a request for the bio-information.

The processor may, from among the one or more peaks, extract, as a first feature, a force value or a differential value at a point corresponding to a smallest force, extract, as a second feature, a force value or a differential value at a point at which the differential value is largest, and extract, as a third feature, a force value or a differential value at a point corresponding to a greatest force.

The processor may obtain the bio-information based on the extracted one or more features and a predefined formula.

The bio-information may include information about one or more of blood pressure, vascular age, a degree of arteriosclerosis, aortic pressure waveform, vascular compliance, stress index, and a degree of fatigue.

The apparatus may further include an outputter configured to output the bio-information.

According to an aspect of another exemplary embodiment, there is provided a method of obtaining bio-information, including: emitting multi-wavelength light to an object; detecting the multi-wavelength light reflected from the object; obtaining a change in volume of a blood vessel based on a quantity of the detected multi-wavelength light and absorbance coefficients of respective wavelengths; and obtaining the bio-information based on the change in volume of the blood vessel.

The obtaining the change in volume of the blood vessel may include obtaining the change in volume of the blood vessel based on a difference between a value, obtained by multiplying a quantity of detected light of a first wavelength of the multi-wavelength light by a ratio of an absorbance coefficient of the first wavelength and an absorbance coefficient of a second wavelength of the multi-wavelength light, and a quantity of light of the second wavelength.

The obtaining the change in volume of the blood vessel may include differentiating, with respect to time, the difference between the value obtained by multiplying the quantity of detected light of the first wavelength by the ratio of the absorbance coefficient of the first wavelength and the absorbance coefficient of the second wavelength and obtaining the change in volume of the blood vessel based on a differential value.

The obtaining the bio-information may include detecting one or more peaks based on the differential value.

The obtaining the bio-information may further include extracting one or more features based on the detected one or more peaks and force information about a force applied to a pulse wave sensor by the object.

The obtaining the bio-information may include obtaining the bio-information based on the extracted one or more features and a predefined formula.

BRIEF DESCRIPTION OF THE DRAWINGS

The above and/or other aspects will become apparent and more readily appreciated by describing certain exemplary embodiments with reference to the accompanying drawings, in which.

DETAILED DESCRIPTION

Figure 1:
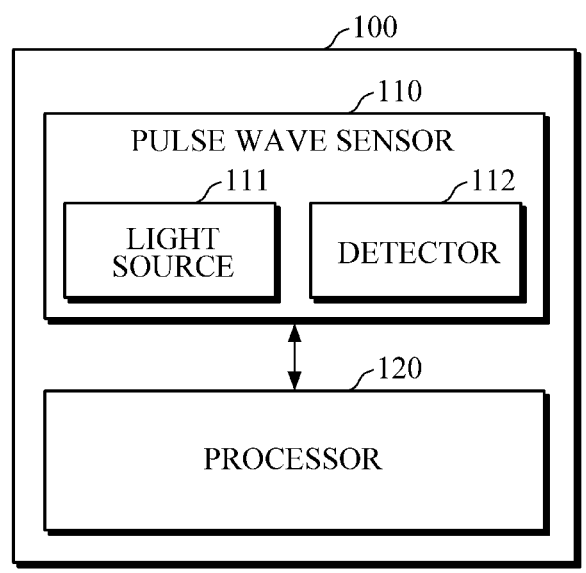
FIGS. 1 to 3 are block diagrams illustrating an apparatus for measuring bio-information according to embodiments.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail. Throughout the drawings and the detailed description, unless otherwise described, the same drawing reference numerals will be understood to refer to the same elements, features, and structures. The relative size and depiction of these elements may be exaggerated for clarity, illustration, and convenience.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

Hereinafter, embodiments of an apparatus and a method for measuring bio-information will be described in detail with reference to the accompanying drawings.

Figure 2:
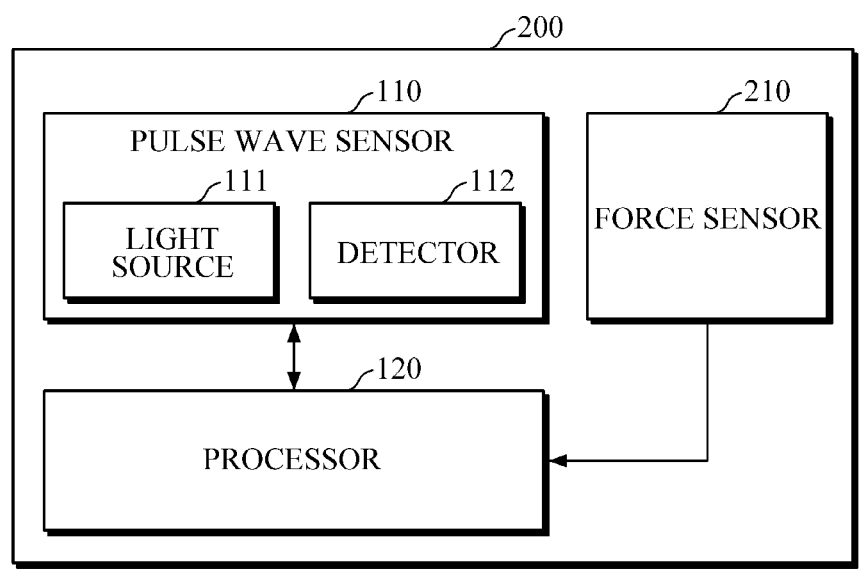
Figure 3:
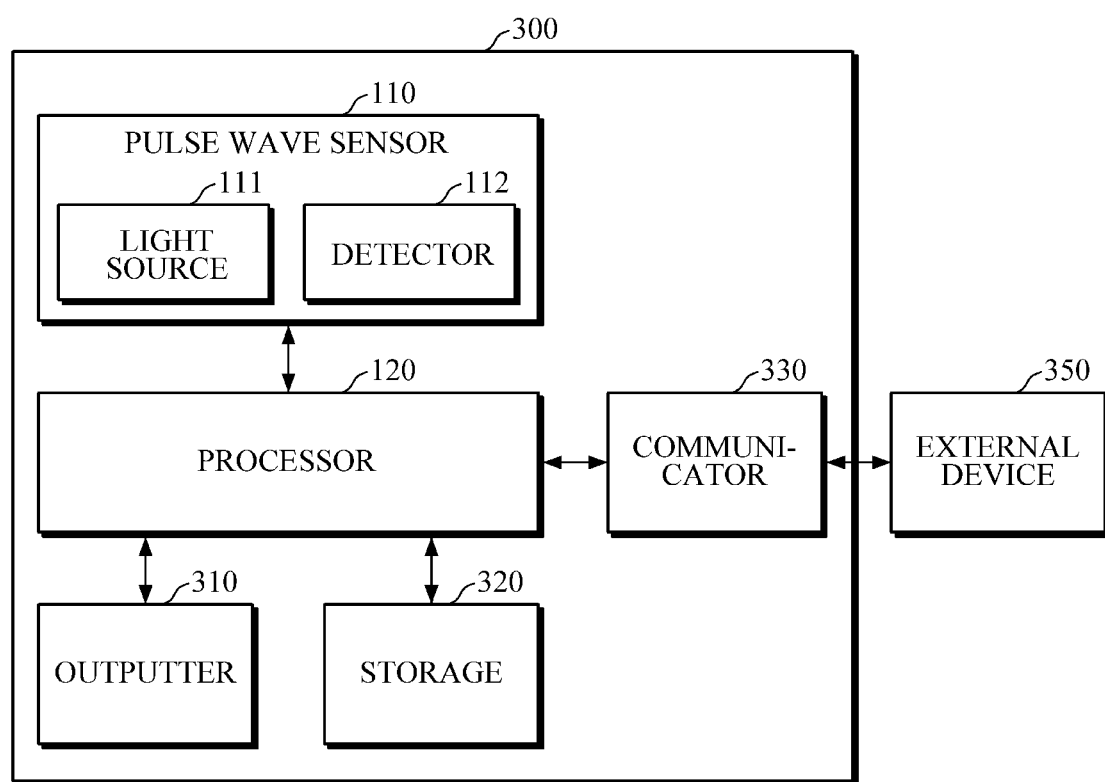

FIGS. 1 to 3 are block diagrams illustrating an apparatus for measuring bio-information according to embodiments. An apparatus 100, an apparatus 200, and an apparatus 300 for measuring bio-information according to various embodiments will be described with reference to FIGS. 1 to 3. Various embodiments of the apparatus for measuring bio-information described hereinafter may be mounted on a device, such as a portable wearable device, a smart device, or the like. For example, the device may include, but not limited to, a wearable device of various types, such as a smart watch worn on the wrist, a smart band type, a headphone-type, a hairband-type, and the like, and a mobile device, such as a smartphone, a tablet personal computer (PC), or the like.

Referring to FIG. 1, the apparatus 100 for measuring bio-information includes a pulse wave sensor 110 and a processor 120.

The pulse wave sensor 100 measures a photoplethysmography (PPG) signal (or referred to as a "pulse wave signal") from an object of interest. The pulse wave sensor 100 may include a light source 111 configured to emit multi-wavelength light to the object of interest and a detector 112 configured to detect multi-wavelength light scattered or reflected from the skin surface or living tissue, such as a blood vessel, of the object of interest irradiated by the light source 111. The light source 111 may be formed as a light emitting diode (LED), a laser diode (LD), or a phosphor, but is not limited thereto. The light source 111 may be formed as one array or two or more arrays. The light source 111 may emit light of a plurality of different wavelengths. The detector 112 may be formed as a photodiode, a phototransistor (PTr), an image sensor (e.g., complementary metal-oxide-semiconductor (CMOS) image sensor), or the like, but is not limited thereto. A plurality of light sources may be arranged at different distances from the detector 112.

The processor 120 may obtain bio-information based on a quantity of multi-wavelength light detected by the pulse wave sensor 110. In this case, the bio-information may include one or more of blood pressure, vascular age, a degree of arteriosclerosis, aortic pressure waveform, vascular compliance, stress index, and a degree of fatigue.

For example, the processor 120 may obtain a change in volume of a blood vessel based on one or more of the quantity of detected multi-wavelength light and an absorbance coefficient for each wavelength and obtain bio-information based on the change in volume of a blood vessel. For example, the processor 120 may differentiate a difference between a value obtained by multiplying a quantity of light of a first wavelength by the ratio of the absorbance coefficients of the first wavelength and a second wavelength (e.g., long wavelength) and a quantity of light of the second wavelength with respect to time and monitor the change in volume of a blood vessel based on the differential value. The processor 120 may generate a graph of the differential value against time and use the generated graph to monitor a time interval during which the volume of blood vessel is changed in association with a change in transmural pressure. In this case, the first wavelength may be a relatively short wavelength of multi-wavelength light, compared to the second wavelength, and the second wavelength may be a relatively long wavelength compared to the first wavelength.

The processor 120 may detect a peak from the interval during which a drastic volume change of the inner blood vessel occurs and obtain the bio-information using the detected peak. In this case, a point at which the above-described differential value is greater than a first threshold and a sharpness is greater than a second threshold may be detected as a peak. For example, the processor 120 may calculate a cosine value of an angle formed between a second point and a third point, which are respectively on the left and right of a first point where the differential value is greater than the first threshold, as the sharpness at the first point. The first threshold and the second threshold may be pre-defined.

The processor 120 may extract one or more features based on one or more detected peaks and obtain the bio-information by inputting the one or more extracted features to a pre-defined bio-information obtaining formula.

Referring to FIG. 2, an apparatus 200 for measuring bio-information may further include a force sensor 210 in addition to the pulse wave sensor 100 and the processor 120.

The force sensor 210 may be mounted inside a main body of the apparatus 200 and may be attached to a surface opposite to a surface where the pulse wave sensor 110 is in contact with an object of interest. The force sensor 210 may measure force information about a force which is applied to the pulse wave sensor 110 by the object while the pulse wave sensor 110 is measuring a pulse wave signal.

The processor 120 may obtain a change in volume of a blood vessel based on one or more of a quantity of detected multi-wavelength light and an absorbance coefficient for each wavelength and obtain bio-information based on the change in volume of a blood vessel. For example, the processor 120 may differentiate a difference between a quantity of light of a first wavelength, multiplied by the ratio of the absorbance coefficients of the first wavelength and a second wavelength, and a quantity of light of the second wavelength with respect to time and detect a peak based on the differential value.

In addition, the processor 120 may extract one or more features based on the one or more detected peaks and force information measured by the force sensor 210. The processor 120 may extract, from among the detected peaks, a force value or a differential value at a point corresponding to the smallest force as a first feature, a force value or a differential value at a point corresponding to the largest differential value as a second feature, and a force value or a differential value at a point corresponding to the greatest force as a third feature.

Referring to FIG. 3, an outputter 310, a storage 320, and a communicator 330 may be further included in addition to the pulse wave sensor 110 and the processor 120. In an exemplary embodiment, the force sensor 210 included in the apparatus 200 shown in FIG. 2 may be further included.

Figure 4A:
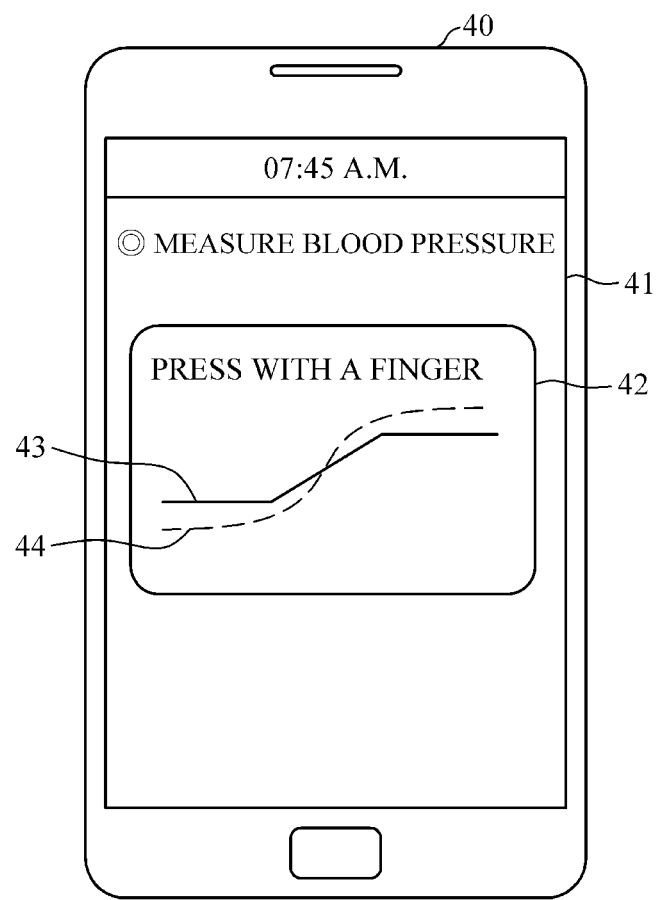
FIGS. 4A and 4B are diagrams illustrating embodiments in which information is provided to a user.

When a request for measuring bio-information is received, the outputter 310 under the control of the processor 110 may provide guidance information about a magnitude of a force to be applied to the pulse wave sensor 110 by the object. For example, FIG. 4A illustrates an embodiment in which an apparatus 300 in the form of a smartphone for measuring bio-information provides guidance information to a user. The outputter 310 may output display data for providing the guidance information and may visually display the guidance information on an area 42 of the display 41. For example, upon receiving a request for measuring bio-information, the outputter 310 may output a visual indication 43 to the user about the magnitude of a force to be applied to the pulse wave sensor 110 by the object. In addition, when the user brings the object of interest into contact with the pulse wave sensor 110 and applies a force to the pulse wave sensor 110 according to the guidance information, an indication 44 of the magnitude of a force actually being applied to the pulse wave sensor 110 by the object while the pulse wave sensor 110 is measuring a pulse wave signal may be visually output. However, the embodiment is not limited to the above example.

Figure 4B:
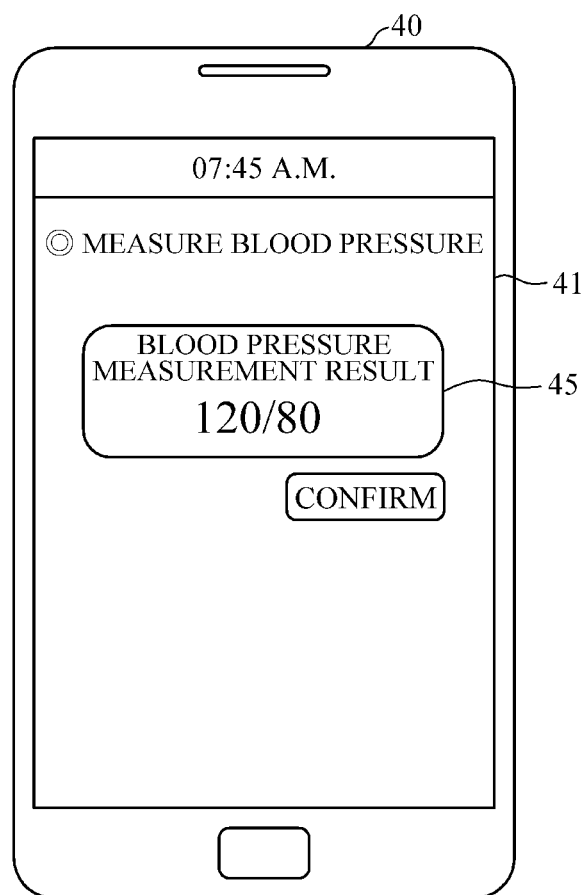

In addition, the outputter 310 may output the pulse wave signal measured by the pulse wave sensor 110 and/or a processing result of the processor 120. For example, FIG. 4B illustrates an embodiment in which the apparatus 300 in the form of a smartphone for measuring bio-information provides a blood pressure measurement result to the user. When blood pressure measurement is completed in the processor 120, the outputter 310 may output display data for providing a blood pressure measurement to a display 41 and visually display the blood pressure measurement value on an area 45 of the display 41. In addition, the outputter 310 may output warning information along with the blood pressure measurement value when the blood pressure measurement result is determined to fall out of a normal range. For example, the blood pressure measurement result may be output in a manner such that the blood pressure measurement result is visually distinguishable from a normal state and the warning information may be output using a non-visual method, such as voice, vibration, tactile sensation, or the like, through a speaker module (or a speaker), a haptic module (or a haptic motor), or the like.

The pulse wave signal, force information, and/or bio-information measurement result may be stored in the storage 320 under the control of the processor 120. In addition, a variety of reference information to be referred to by the processor 120 may be stored in the storage 320. Here, the reference information may include information about a bio-information obtaining formula, a cuff blood pressure for calibration of the bio-information obtaining formula, a threshold for detecting a peak, and the like. In addition, the reference information may include user characteristic information, such as age, sex, health status, and the like of the user.

In this case, the storage 320 may include a storage medium of at least one type of a flash memory type, a hard disk type, a multimedia card micro type, a card type memory (e.g., SD or XD memory), random access memory (RAM), static random access memory (SRAM), read-only memory (ROM), electrically erasable programmable read-only memory (EEPROM), magnetic memory, magnetic disk, and optical disk.

The communicator 330 may be connected to an external device 350 through a communication technology and transmit and receive a variety of information to and from the external device. Information received from the external device 350 may be stored in the storage 320. In this case, the external device 350 may include a smartphone, a tablet personal computer (PC), a notebook PC, a desktop PC, a cuff-type blood pressure measurement apparatus, and the like, but is not limited thereto. In this case, the communication technology may include, but not limited to, Bluetooth communication, Bluetooth low energy (BLE) communication, near field communication (NFC), wireless local access network (WLAN) communication, ZigBee communication, infrared data association (IrDA) communication, Wi-Fi direct (WFD) communication, ultra-wideband (UWB) communication, Ant+ communication, Wi-Fi communication, and mobile communication.

For example, when the processor 102 obtains bio-information, the communicator 330 may transmit a bio-information measurement result to the external device 350 having a relatively excellent computing performance. In this case, the external device 350 may output the bio-information measurement result to the user through an output module or manage a history of a variety of bio-information. The communicator 330 may receive a cuff blood pressure from a cuff-type blood pressure measurement apparatus and receive reference information from another external device 350.

FIGS. 5A to 5K are diagrams for describing measurement of bio-information. Embodiments in which the processor 120 of the apparatuses 100, 200, and 300 for measuring bio-information measures bio-information, for example, blood pressure will be described with reference to FIGS. 5A to 5K.

Figure 5A:
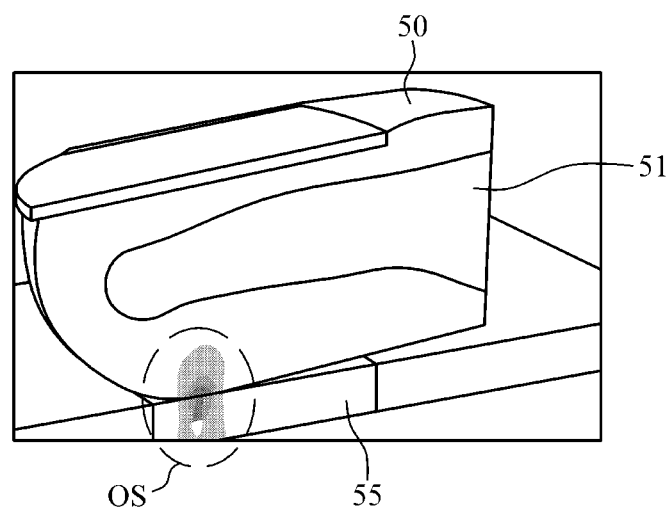
FIGS. 5A to 5K are diagrams for describing measurement of bio-information.
Figure 5B:
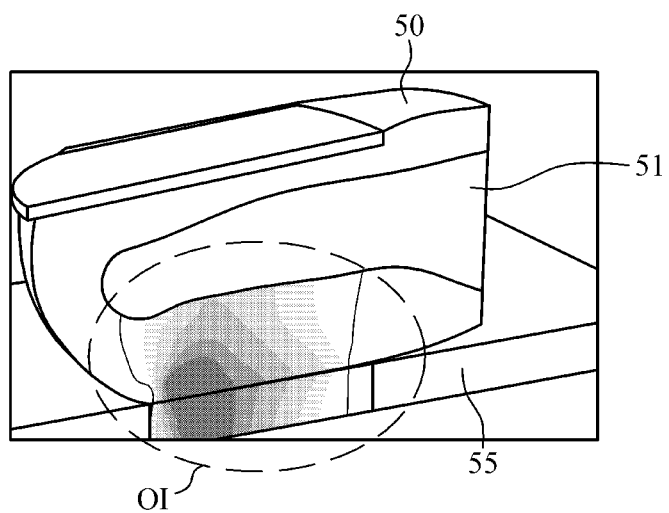

FIGS. 5A and 5B illustrate a state in which a finger 50 presses a pulse wave sensor 55. As shown in FIG. 5A, when the pulse wave sensor 55 is softly pressed by the finger 50, a stress is first exerted on a skin surface OS of the finger 50. Then, as shown in FIG. 5B, as the strength of the force pressing the pulse wave sensor 55 is gradually increased, a stress inside the finger 50 is transferred to tissues OI under a finger bone 51. Generally, there are capillaries on the skin surface of the finger, arterioles deeper within the finger, and an artery further deeper within the finger. Therefore, when the strength of the force of the finger 50 pressing the pulse wave sensor 55 is gradually increased, the stress is exerted on the capillaries, the arterioles, and the artery in the order described.

Figure 5C:
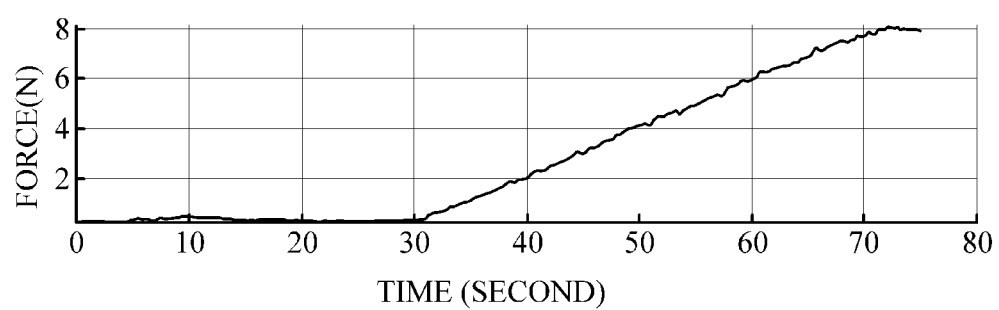
Figure 5D:
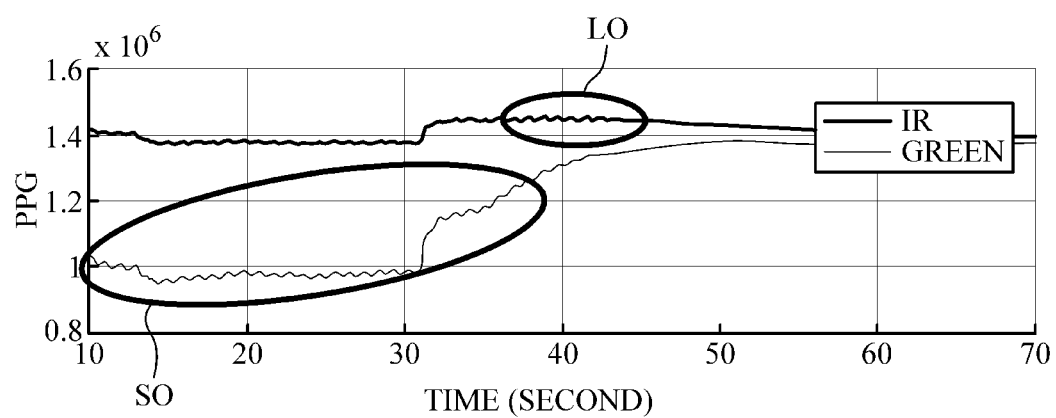

FIG. 5C is a graph showing an increase of a force applied to a pulse wave sensor by an object with time. FIG. 5D is a graph showing signals of each wavelength obtained by a pulse wave sensor at the time of increasing the strength of a finger pressing the pulse wave sensor. As shown in the drawings, a green wavelength, which is a relatively short wavelength, penetrates a shallow portion of the skin, so that a pulse wave signal at the green wavelength is relatively strongly detected at a portion SO where a force of the finger is weak. In addition, when the force of the finger pressing the pulse wave sensor is gradually increased, the pulse wave signal at the green wavelength stops being detected at a pertinent portion LO whereas a signal at the infrared (IR) wavelength, which is a long wavelength, is relatively strongly detected.

In other words, referring to FIGS. 5C and 5D, a phenomenon occurring inside the finger when the force of the finger pressing the pulse wave sensor is increased from 0 N to 8 N is as follows. First, as a stress on the skin surface of the finger increases, an external pressure applied to the capillaries is gradually increased, and accordingly the capillaries are closed so that the blood flow into the capillaries is reduced. A pulse wave signal at the green wavelength gradually decreases after 40 seconds, at which point the strength of the force is gradually increased. Thereafter, when the force pressing the pulse wave sensor is gradually increased around at 40 seconds, the capillaries are closed so that reflective waves toward the arterioles are increased and the stress around the arterioles is increased, which causes an increase of external pressure on the arterioles. Accordingly, the external pressure on the arterioles becomes close to an internal pressure inside the arterioles so that the transmural pressure becomes close to zero. That is, the pulse wave at the infrared wavelength becomes larger. When the force pressing the pulse wave sensor is further increased at around 50 seconds, the external pressure on the arterioles becomes greater than the internal pressure. Accordingly, the pulse wave of arterioles gradually decreases, thereby causing a decrease in the pulse wave signal at the infrared wavelength.

As described above, as the pressure decreases from the aorta to the peripheral blood vessels, oscillation in vascular pressure also decreases. Therefore, in order to accurately measure the blood vessels, pulse wave signals need to be measured in the arteriole or the artery, that is, a blood vessel as close as possible to the aorta, rather than in the capillary vessel, and thereby bio-information can be accurately measured.

Figure 5E:
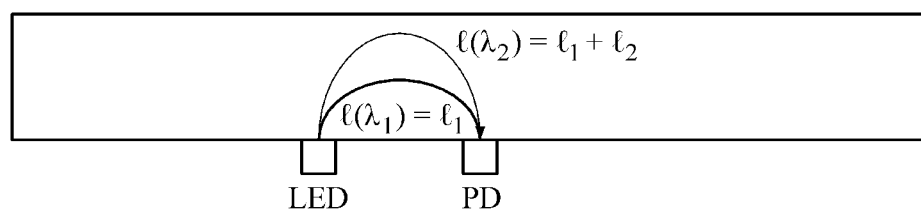

Referring to FIG. 5E, assuming that a first wavelength $\lambda_1$ is shorter than a second wavelength $\lambda_2$, $\ell_1$ is a physical distance of an effective pathway of light of the first wavelength, and $\ell(\lambda_2)$ is a physical distance of an effective pathway of light of the second wavelength, $\ell(\lambda_2)$ may be expressed as Equation 1 shown below. Here, $\ell_2$ may denote a pathway having an arbitrary physical distance longer than $\ell_1$.

$$\ell_{(\lambda_2)} = \ell_1 + \ell_2 \qquad (1)$$

The processor 120 may derive Equation 2 as shown below by applying the Beer-Lambert law. Here, I denotes transmitted light, $I_0$ denotes incident light, $$\frac{I(\lambda_1)}{I_0};$$

denotes a quantity of detected light of the first wavelength, and $$\frac{I(\lambda_2)}{I_0};$$

denotes a quantity of detected light of the second wavelength. In addition, $\varepsilon$ denotes an absorbance coefficient, $\varepsilon_1$ denotes an absorbance coefficient of the first wavelength, and $\varepsilon_2$ denotes an absorbance coefficient of the second wavelength.

$$\ln \frac{I(\lambda_1)}{I_0} = -\varepsilon_1 c_1 \ell_1 \quad (2)$$

$$\ln \frac{I(\lambda_2)}{I_0} = -\varepsilon_2 c_2 (\ell_1 + \ell_2)$$

Since a pulsatile component is a matter of concern for the measurement of blood pressure, it is assumed that absolute amounts c, $c_1$, and $c_2$ of effective absorbance material, which is varied in the aorta, the arterioles, and the capillaries when a pulse occurs, are equal to one another. That is, theoretically, the amount of blood flowing out of the blood vessels and the amount of blood flowing into the blood vessels are the same, and thus the amount of effective absorbance material in a single aorta may vary but the total amount of effective absorbance materials may be constant. Under this assumption, the processor 102 may derive Equation 3 shown below from the above Equation 2.

$$\frac{\varepsilon_2}{\varepsilon_1} \ln \frac{I(\lambda_1)}{I_0} = -\varepsilon_2 c \ell_1 \quad (3)$$

$$\varepsilon_2 c \ell_2 = \frac{\varepsilon_2}{\varepsilon_1} \ln \frac{I(\lambda_1)}{I_0} - \ln \frac{I(\lambda_2)}{I_0}$$

Since $\varepsilon_1$, $\varepsilon_2$, and $\ell_1$ when a pulse occurs are constants, assuming that the amount c of effective absorbance material is varied according to the pulse, a pulse of the blood vessels deeper than the skin surface may be observed using Equation 3 based on three values, that is, the quantity of light of the first wavelength reflected from the skin surface, the quantity of light of the second wavelength reflected from the deeper skin, and the ratio of absorbance coefficients of the two wavelengths.

Figure 5F:
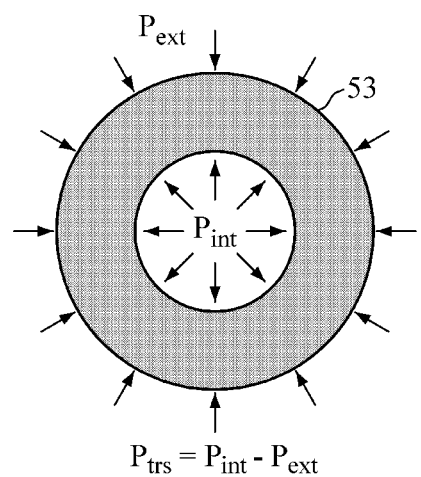

FIG. 5F is a diagram for describing a change in pressure of a blood vessel when a pulse wave sensor is pressed by a finger. Referring to FIG. 5F, when the pulse wave sensor is gradually strongly pressed by the finger, the force is transferred to a blood vessel 53. As the force is increased, an external pressure $P_{ext}$ on the blood vessel increases and gradually becomes equal to an internal pressure $P_{int}$, causing the transmural pressure $P_{trs}$ to become zero. At this time, an effective blood vessel has a maximum blood vessel expansion rate.

For convenience of description, $\varepsilon_2 c \ell_2$ in Equation 3 is denoted as L(t). When L(t) is differentiated with respect to the transmural pressure $P_{trs}$, a relation as shown below in Equation 4 may be derived since there is a correlation between the volume of a blood vessel and the concentration of blood.

$$\frac{dL(t)}{dp_{trs}} = \varepsilon_2 \ell_2 \frac{dV(t)}{dp_{trs}} \quad (4)$$

When the force of the finger is gradually increased in order to change the transmural pressure, Equation 5(1) shown below may be obtained since the force is proportional with the transmural pressure. When Equation 5(1) is expressed in terms of time, a relation as shown below in Equation 5(2) may be obtained. In this case, assuming that the force is increased with time at a very constant speed, the differentiation of the force with respect to time becomes a specific constant f, and thus a relation as shown below in Equation 5(3) may be derived from Equation 4.

$$(1) \; \frac{dL(t)}{dp_{trs}} = \frac{dL(t)}{dF} \quad (5)$$

$$(2) \; \frac{dL(t)}{dF} = \frac{dL(t)}{dt} \frac{dt}{dF}$$

$$(3) \; \varepsilon_2 \ell_2 \frac{dV(t)}{dp_{trs}} = \frac{dL(t)}{dt} f$$

In other words, when the quantity of light of the first wavelength and the quantity of light of the second wavelength are detected by the pulse wave sensor 110, the processor 102 may obtain a change in volume inside the blood vessel in association with a change in the transmural pressure applied to the blood vessel by multiplying the quantity of light of the first wavelength by the ratio of the absorbance coefficients and differentiating a difference between the multiplied result and the quantity of light of the second wavelength with respect to time.

In this case, since the ratio $$\frac{\varepsilon_2}{\varepsilon_1}$$

of the absorbance coefficients is a specific constant, which does not change with the pulse, an arbitrary constant value may be input. For example, the user-specific ratio value of absorbance coefficients may be preset to an optimal parameter value determined for each individual through a fluorescence experiment. The determined optimal parameter value may be stored in the storage 320 and be referred to by the processor 120.

Figure 5G:
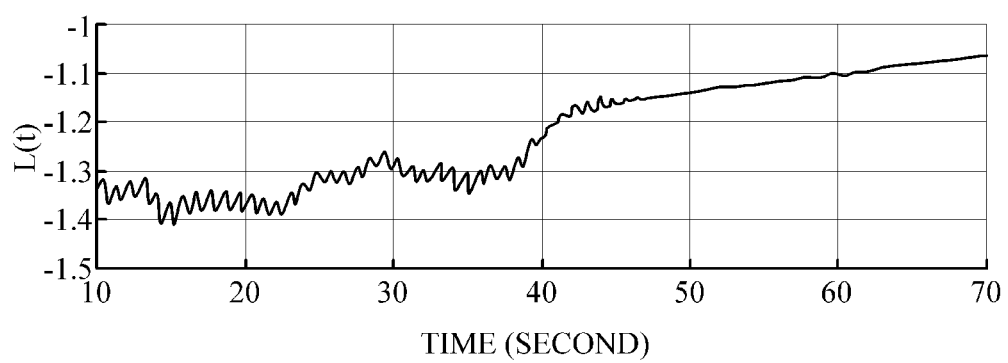
Figure 5H:
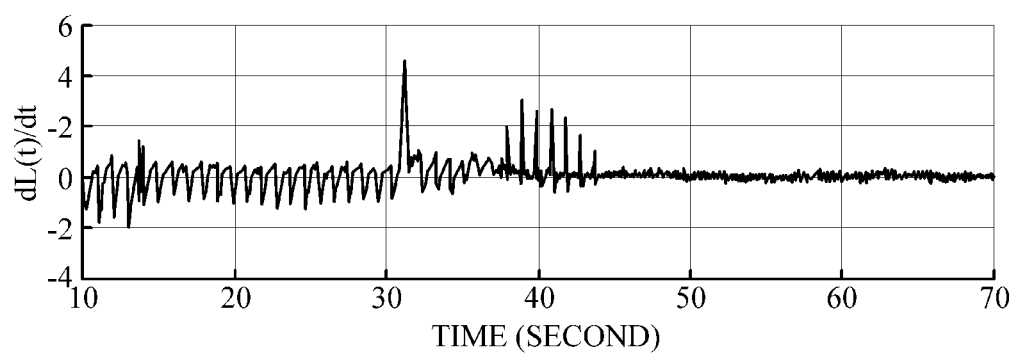

FIG. 5G is a graph of L(t) derived as shown in the above Equation, and FIG. 5H is a graph showing $$\frac{dL(t)}{dt}$$

obtained by differentiating L(t) with respect to time. According to Equation 5(3), the increase of transmural pressure $P_{trs}$ increases volume, and thus values of $$\frac{dL(t)}{dt}$$

that are less than 0 may be negligible. This is because when the pulse occurs, the internal pressure $P_{int}$ increases and acts away from the inside of the blood vessel and toward the outside.

Figure 5I:
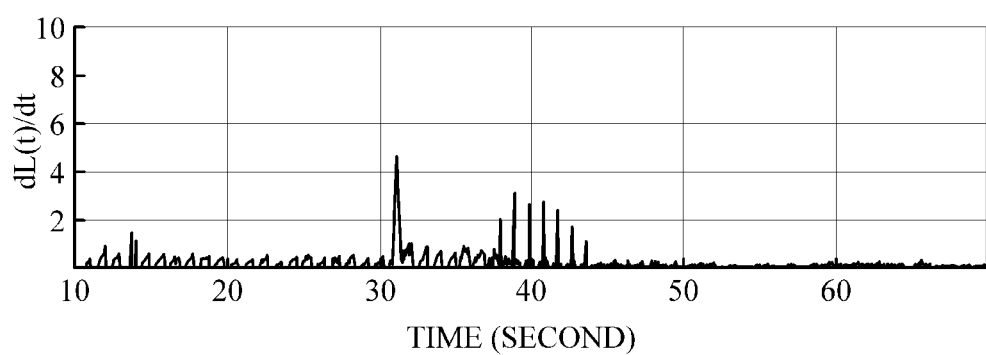

FIG. 5I is a graph showing values of $$\frac{dL(t)}{dt}$$

that are greater than 0. Referring to FIG. 5I, it can be seen that during a period between 35 seconds and 45 seconds, the volume of the blood vessel is drastically changed according to the change in transmural pressure. As such, the processor 120 may monitor the change in volume of the blood vessel according to the change of transmural pressure by differentiating L(t) with respect to time. In addition, the processor 120 may detect a peak from the graph obtained by differentiating L(t) with respect to time. In FIG. 5I, a point in an interval between 35 seconds and 45 seconds is detected as a peak.

The processor 120 may detect a point at which a differential value dL(t) satisfies predetermined conditions. For example, when a differential value dL(t) at a specific point is (1) a maximum value within a predetermined time interval, is (2) greater than a first threshold, and has (3) a sharpness greater than a second threshold, the specific point may be determined as a peak. In this case, it may be predetermined that a peak is determined only when all conditions (1), (2), and (3) are satisfied, but the embodiment is not limited thereto. For example, at least one of conditions (2) and (3) may be omitted, and various additional conditions may be set.

Figure 5J:
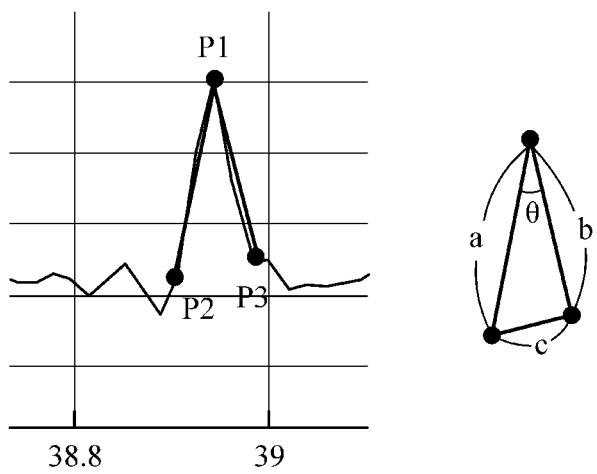

The sharpness as condition (3) may be determined based on an angle θ formed between a second point P2 and a third point P3, which are on the left and right of a first point P1, as shown in FIG. 5J. For example, the processor 120 may calculate a cosine value for the angle θ of the first point P1 using Equation 6 below, and compare the calculated cosine value with the predefined second threshold.

$$\cos\theta = \frac{-c^2 + a^2 + b^2}{2ab} \tag{6}$$

Figure 5K:
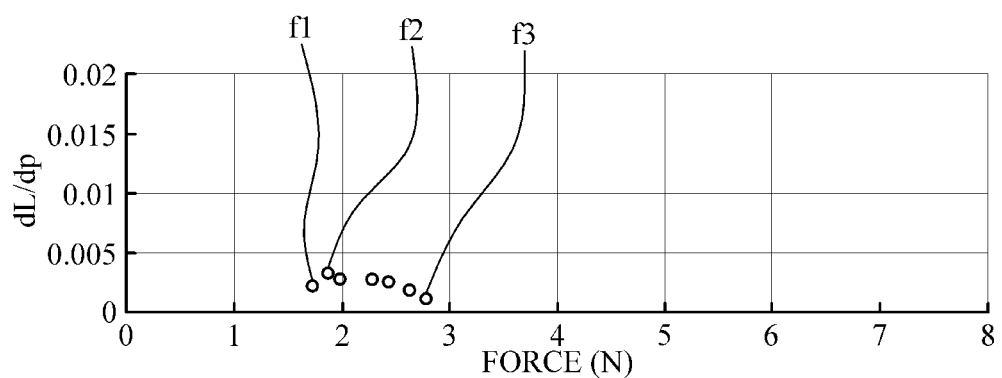

When one or more peaks are detected, the processor 120 may extract one or more features to be used for measuring blood pressure based on the one or more detected peaks. For example, FIG. 5K is a graph showing a relationship between the above-described differential value and a force. The processor 102 may generate a graph as shown in FIG. 5K based on the differential value calculated with reference to time during the measurement of a pulse and corresponding force information, and extract one or more features from the generated graph.

For example, the processor 120 may extract, as a first feature, a force value or a differential value at a point f1 which corresponds to the smallest force from among the detected peaks. In addition, the processor 120 may extract, as a second feature, a force value or a differential value at a point f2 which corresponds to the largest differential value. Also, the processor 120 may extract, as a third feature, a force value or a differential value at a point f3 which corresponds to the greatest force. However, these are merely examples, and features may be extracted according to other criteria.

When one or more features f1, f2, and f3 are extracted, the processor 120 may obtain blood pressure by applying the features to a predefined formula, as shown in Equation 7. In this case, formulas for mean blood pressure (MBP), systolic blood pressure (SBP), and diastolic blood pressure (DBP) may be defined differently from each other. In addition, the formulas may be defined in various forms, such as a linear function, a regression formula, an artificial neural network, artificial intelligence, and the like.

$$SBP=f(f1,f2,f3)$$

$$DBP=f(f1,f2,f3)$$

$$MBP=f(f1,f2,f3) \tag{7}$$

As described above, according to the disclosed embodiments, it is possible to extract a pulsation signal at a specific depth in the object of interest through multi-wavelength pulse wave signals detected by the pulse wave sensor 110 and measure bio-information, such as blood pressure, using the extracted pulsation signal.

Figure 6:
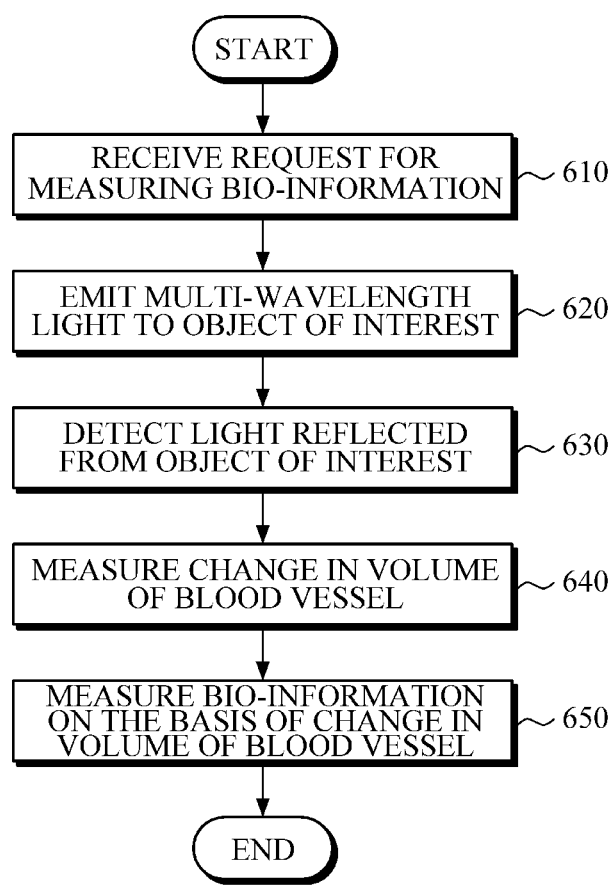
FIG. 6 is a flowchart illustrating a method of measuring bio-information according to one embodiment.

FIG. 6 is a flowchart illustrating a method of measuring bio-information according to one embodiment.

The method shown in FIG. 6 is one embodiment of a method of measuring bio-information which is performed by the apparatuses 100, 200, and 300 for measuring bio-information according to the embodiments of FIGS. 1 to 3.

Referring to FIG. 6, the apparatus for measuring bio-information may receive a request for measuring bio-information, in 610. The request for measuring bio-information may be input by a user. Alternatively, when information about an interval for measuring bio-information is preset, a request for measuring bio-information may be automatically issued at the corresponding interval.

Then, multi-wavelength light may be emitted to an object of interest in 620, and multi-wavelength light reflected or scattered from the object may be detected in 630. A pulse wave sensor may include one light source and may sequentially emit light of a different wavelength by adjusting a wavelength of the light source. Alternatively, the pulse wave sensor may include a plurality of light sources and each light source may emit light of a different wavelength. The pulse wave sensor may include one or more detectors and detect light of a different wavelength sequentially emitted from the light source. Alternatively, when the pulse wave sensor is configured with an array of a plurality of light sources, the detectors may be formed to correspond to the respective light sources and detect light of a wavelength emitted from the corresponding light source.

Then, a change in volume of a blood vessel may be measured based on the detected multi-wavelength light in 640. For example, the change in volume of the blood vessel may be detected based on one or more of the quantity of detected multi-wavelength light or absorbance coefficients for each wavelength. For example, a difference between a value obtained by multiplying the quantity of light of a first wavelength by the ratio of the absorbance coefficients of the first wavelength and a second wavelength, which is a long wavelength, and the quantity of light of the second wavelength may be differentiated with respect to time, and the change in volume of the blood vessel may be monitored based on the differential value.

Then, bio-information may be measured based on the change in volume of the blood vessel in 650. For example, one or more peaks may be detected based on the differential value described in operation 640. In addition, one or more features may be extracted based on the one or more detected peaks and information about a force exerted on the pulse wave sensor by the object of interest, and the bio-information may be measured using the extracted features. For example, when one or more features are extracted, the bio-information may be measured by applying the extracted features to a predefined bio-information obtaining formula.

The exemplary embodiments can be implemented as computer readable codes in a computer readable record medium. Codes and code segments constituting the computer program for implementing the exemplary embodiments can be easily inferred by a skilled computer programmer in the art in light of the disclosure. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

At least one of the components, elements, modules or units described herein may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in block diagrams, communication between the components, elements or units may be performed through the bus. Functional aspects of the above exemplary embodiments may be implemented in algorithms that execute on one or more processors. Furthermore, the components, elements or units represented by a block or processing operations may employ any number of related art techniques for electronics configuration, signal processing and/or control, data processing and the like.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for obtaining bio-information, comprising:
   a pulse wave sensor comprising a light source and a detector, the light source configured to emit multi-wavelength light to an object, the detector configured to detect the multi-wavelength light reflected from the object;
   a force sensor configured to acquire a force information about a force applied to the pulse wave sensor by the object; and
   a processor configured to:
   obtain a change in volume of a blood vessel based on a difference between a value, obtained by multiplying a quantity of detected light of a first wavelength of the multi-wavelength light by a ratio of an absorbance coefficient of the first wavelength and an absorbance coefficient of a second wavelength of the multi-wavelength light, and a quantity of detected light of the second wavelength;
   extract one or more features based on the change in volume of the blood vessel, and the force information about a force applied to the pulse wave sensor by the object; and
   obtain the bio-information based on the extracted one or more features and a predefined formula.

2. The apparatus of claim 1, wherein the processor is further configured to differentiate, with respect to time, the difference between the value, obtained by multiplying the quantity of detected light of the first wavelength by the ratio of the absorbance coefficient of the first wavelength and the absorbance coefficient of the second wavelength, and the quantity of detected light of the second wavelength, and obtain the change in volume of the blood vessel based on a differential value.

3. The apparatus of claim 2, wherein the processor is further configured to generate a graph of the differential value against time and monitor a time interval during which the volume of the blood vessel is changed according to a change in transmural pressure.

4. The apparatus of claim 2, wherein the processor is further configured to detect one or more peaks based on the differential value and obtain the bio-information using the detected one or more peaks.

5. The apparatus of claim 4, wherein the processor is further configured to detect, as a peak, a point at which the differential value is greater than a first threshold and a sharpness is greater than a second threshold.

6. The apparatus of claim 5, wherein the processor is further configured to determine, as a sharpness at a first point, determine a cosine value of an angle, formed between a second point and a third point, the second point and the third point being on a left and a right of the first point.

7. The apparatus of claim 4, wherein the processor is further configured to extract the one or more features based on the detected one or more peaks and the force information.

8. The apparatus of claim 7, wherein the processor is further configured to provide guidance information about a magnitude of force to be applied to the pulse wave sensor in response to a request for the bio-information.

9. The apparatus of claim 7, wherein the processor is further configured to, from among the one or more peaks, extract, as a first feature, a force value or a differential value at a point corresponding to a smallest force, extract, as a second feature, a force value or a differential value at a point at which the differential value is largest, and extract, as a third feature, a force value or a differential value at a point corresponding to a greatest force.

10. The apparatus of claim 1, wherein the bio-information comprises information about one or more of blood pressure, vascular age, a degree of arteriosclerosis, aortic pressure waveform, vascular compliance, stress index, and a degree of fatigue.

11. The apparatus of claim 1, further comprising an outputter configured to output the bio-information.

12. A method of obtaining bio-information, comprising:
   emitting multi-wavelength light to an object;
   detecting the multi-wavelength light reflected from the object;
   acquiring a force information about a force applied to a pulse wave sensor by the object;

obtaining a change in volume of a blood vessel based on a difference between a value, obtained by multiplying a quantity of detected light of a first wavelength of the multi-wavelength light by a ratio of an absorbance coefficient of the first wavelength and an absorbance coefficient of a second wavelength of the multi-wavelength light, and a quantity of detected light of the second wavelength;

extracting one or more features based on the change in volume of the blood vessel, and the force information about a force applied to the pulse wave sensor by the object; and obtaining the bio-information based on the extracted one or more features and a predefined formula.

13. The method of claim 12, wherein the obtaining the change in volume of the blood vessel comprises differentiating, with respect to time, the difference between the value obtained by multiplying the quantity of detected light of the first wavelength by the ratio of the absorbance coefficient of the first wavelength and the absorbance coefficient of the second wavelength and obtaining the change in volume of the blood vessel based on a differential value.

14. The method of claim 13, wherein the obtaining the change in volume of the blood vessel comprises generating a graph of the differential value against time and monitoring a time interval during which the volume of the blood vessel is changed according to a change in transmural pressure.

15. The method of claim 13, wherein the obtaining the bio-information comprises detecting one or more peaks based on the differential value.

16. The method of claim 15, wherein the detecting the one or more peaks based on the differential value comprises detecting as a peak, a point at which the differential value is greater than a first threshold and a sharpness is greater than a second threshold.

17. The method of claim 16 further comprising determining, as a sharpness at a first point, determining a cosine value of an angle, formed between a second point and a third point, the second point and the third point being on a left and a right of the first point.

18. The method of claim 15, wherein the obtaining the bio-information further comprises extracting the one or more features based on the detected one or more peaks and the force information.

19. The method of claim 18, further comprising providing guidance information about a magnitude of force to be applied to the pulse wave sensor in response to a request for the bio-information.

20. The method of claim 18, wherein the extracting the one or more features based on the detected one or more peaks and the force information comprising from among the one or more peaks, extracting as a first feature, a force value or a differential value at a point corresponding to a smallest force, extracting as a second feature, a force value or a differential value at a point at which the differential value is largest, and extracting as a third feature, a force value or a differential value at a point corresponding to a greatest force.

* * * * *